United States Patent [19]

Förster et al.

[11] Patent Number: 5,780,392
[45] Date of Patent: Jul. 14, 1998

[54] HETEROCYCLYL-1,3,4-THIADIAZOLYLOXYACETAMIDES AND THEIR USE AS HERBICIDES

[75] Inventors: Heinz Förster, Kadenbach; Hans-Joachim Diehr, Wuppertal; Hans-Joachim Santel; Markus Dollinger, both of Leverkusen, all of Germany

[73] Assignee: Bayer Aktiengesellschaft, Leverkusen, Germany

[21] Appl. No.: 721,981

[22] PCT Filed: Mar. 29, 1995

[86] PCT No.: PCT/EP95/01174
  § 371 Date: Oct. 4, 1996
  § 102(e) Date: Oct. 4, 1996

[87] PCT Pub. No.: WO94/27711
  PCT Pub. Date: Oct. 19, 1995

[30] Foreign Application Priority Data

Apr. 11, 1994 [DE] Germany .................. 44 12 328.0

[51] Int. Cl.[6] .................. C07D 417/04; A01L 43/824
[52] U.S. Cl. .................. 504/263; 540/603; 544/134; 546/165; 546/269; 546/277; 548/136
[58] Field of Search .................. 548/136; 546/209, 546/165, 277; 544/134; 540/603; 504/263

Primary Examiner—Robert Gerstl
Attorney, Agent, or Firm—Sprung Kramer Schaefer & Briscoe

[57] ABSTRACT

This invention concerns heterocyclyl-1,3,4-thiadiazolyloxycetamides of the formula

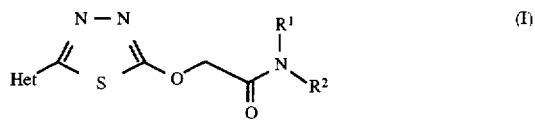

in which $R^1$ is hydrogen or optionally substituted alkyl, alkenyl, alkinyl or aralkyl, $R^2$ is optionally substituted alkyl, alkenyl, alkinyl, cycloalkyl, cycloalkenyl, aralkyl, aryl, alkoxy, alkenyloxy or alkinyloxy or $R^1$ and $R^2$, together with the nitrogen atom to which they are bound, form an optionally substituted, saturated or unsaturated nitrogen heterocycle which may contain other hetero-atoms and to which a benzo-grouping can be fused, and Het is an optionally substituted heterocyclyl group with the exception of thienyl. The Invention also concerns a method of preparing such compounds, intermediates used in their preparation and the use of such compounds as herbicides.

8 Claims, No Drawings

HETEROCYCLYL-1,3,4-THIADIAZOLYLOXYACETAMIDES AND THEIR USE AS HERBICIDES

The invention relates to novel heterocyclyl- 1,3,4-thiadiazolyloxyacetamides, to a process and novel intermediates for their preparation and to their use as herbicides.

It is already known that certain thienyl-1,3,4-thiadiazolyloxyacetamides have herbicidal properties (cf. JP-A 05286969, cited in Chem. Abstracts 120: 245115). However, the efficacy of these known compounds is not completely satisfactory in all fields of application, in particular at low application rates and concentrations.

The novel heterocyclyl-1,3,4-thiadiazolyloxyacetamides of the general formula (I) have now been found,

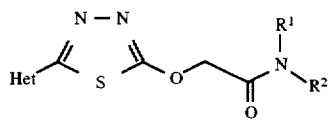
(I)

in which

R$^1$ represents hydrogen or in each case unsubstituted or substituted alkyl, alkenyl, alkinyl or aralkyl, R$^2$ represents in each case unsubstituted or substituted alkyl, alkenyl, alkinyl, cycloalkyl, cycloalkenyl, aralkyl, aryl, alkoxy, alkenyloxy or alkinyloxy, or R$^1$ and R$^2$ together with the nitrogen atom to which they are bound form an unsubstituted or substituted, saturated or unsaturated nitrogen heterocycle which can contain other heteroatoms and to which a benzo grouping can be fused, and Het represents unsubstituted or substituted heterocyclyl with the exception of thienyl.

It has further been found that the novel heterocyclyl-1,3,4-thiadiazolyloxyacetamides of the general formula (I) are obtained if alkylsulphonyl-1,3,4-thiadiazoles of the general formula (II)

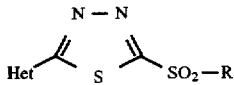
(II)

in which

Het has the meaning given above and

R represents alkyl are reacted with hydroxyacetamides of the general formula (III)

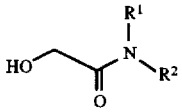
(III)

in which

R$^1$ and R$^2$ have the meaning given above, in the presence or absence of a diluent, in the presence or absence of an acid acceptor and in the presence or absence of a catalyst.

Finally, it has been found that the novel heterocyclyl-1,3,4-thiadiazolyloxyacetamides of the general formula (I) have herbicidal properties of interest.

The invention preferably relates to compounds of the formula (I) in which

R$^1$ represents hydrogen, C$_1$–C$_8$-alkyl (which is optionally substituted by fluorine, chlorine, cyano or C$_1$–C$_4$-alkoxy), C$_2$–C$_8$-alkenyl (which is optionally substituted by fluorine and/or chlorine), C$_2$–C$_8$-alkinyl or benzyl (which is optionally substituted by fluorine, chlorine, C$_1$–C$_4$-alkyl and/or C$_1$–C$_4$-alkoxy), R$^2$ represents C$_1$–C$_8$-alkyl (which is optionally substituted by fluorine, chlorine, cyano or C$_1$–C$_4$-alkoxy), C$_2$–C$_8$-alkenyl (which is optionally substituted by fluorine and/or chlorine), C$_2$–C$_8$-alkinyl, C$_3$–C$_6$-cycloalkyl (which is optionally substituted by chlorine and/or C$_1$–C$_3$-alkyl), C$_5$- or C$_6$-cycloalkenyl, benzyl (which is optionally substituted by fluorine, chlorine, C$_1$–C$_4$-alkyl and/or C$_1$–C$_4$-alkoxy), phenyl (which is optionally substituted by fluorine, chlorine, bromine, iodine, cyano, nitro, C$_1$–C$_4$-alkyl, trifluoromethyl, C$_1$–C$_4$-alkoxy and/or C$_1$–C$_4$-alkylthio), C$_1$–C$_8$-alkoxy (which is optionally substituted by C$_1$–C$_4$-alkoxy), or C$_3$–C$_4$-alkenyloxy, or R$^1$ and R$^2$ together with the nitrogen atom to which they are bound form a saturated or unsaturated five- to seven-membered nitrogen heterocycle which is optionally monosubstituted to trisubstituted by C$_1$–C$_3$-alkyl and can additionally contain oxygen and is optionally benzo-fused, and Het represents saturated or unsaturated, optionally benzo-fused heterocyclyl having 2 to 8 carbon atoms and 1 to 4 heteroatoms - in particular nitrogen, oxygen and/or sulphur atoms, thienyl being excepted and the possible substituents preferably being selected from the following listing:

halogen, cyano, nitro, carboxyl, (in each case optionally halogen-substituted) C$_1$–C$_4$-alkyl, C$_1$–C$_4$-alkoxy, C$_1$–C$_4$-alkylthio, C$_1$–C$_4$-alkylsulphinyl, C$_1$C$_4$-alkylsulphonyl, C$_1$–C$_4$-alkylcarbonyl, C$_1$–C$_4$-alkoxy-carbonyl.

The invention relates in particular to compounds of the formula (I) in which

R$^1$ represents methyl, ethyl, n- or i-propyl, n-, i- or s-butyl, n-, i- or s-pentyl (each of which is optionally substituted by fluorine, chlorine, cyano, methoxy or ethoxy), propenyl, butenyl, propinyl or butinyl, R$^2$ represents methyl, ethyl, n- or i-propyl, n-, i- or s-butyl, n-, i- or s-pentyl, n-, i- or s-hexyl (each of which is optionally substituted by fluorine, chlorine, cyano, methoxy or ethoxy); propenyl, butenyl, pentenyl, propinyl, butinyl or pentinyl; cyclopentyl or cyclohexyl (each of which is optionally substituted by methyl and/or ethyl); cyclohexenyl; benzyl (which is optionally substituted by fluorine, chlorine and/or methyl); or phenyl (which is optionally substituted in each case by fluorine, chlorine, bromine, cyano, nitro, methyl, ethyl, trifluoromethyl, methoxy or ethoxy); methoxy, ethoxy, n- or i-propoxy, n-, i- or s-butoxy, n-, i- or s-pentyloxy (each of which is optionally substituted by methoxy or ethoxy), or R$^1$ and R$^2$ together with the nitrogen atom to which they are bound represent piperidinyl or morpholinyl which is optionally monosubstituted to trisubstituted by methyl and/or ethyl; pyrrolidinyl which is optionally monosubstituted or disubstituted by methyl and/or ethyl; perhydroazepinyl; or 1,2,3,4-tetrahydro(iso)-quinolinyl, and Het represents in each case unsubstituted or substituted furyl, benzofuryl, tetrahydrofuryl, pyrrolyl, benzopyrrolyl, tetrahydropyrrolyl, oxazolyl isoxazolyl, thiazolyl, isothiazolyl, oxadiazolyl, thiadiazolyl, pyridyl, pyrimidyl, triazinyl or tetrahydropyranyl, the possible substituents being selected in particular from the following listing:

fluorine, chlorine, bromine, cyano (in each case optionally fluorine- and/or chlorine-substituted) methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl.

A very particularly preferred group of the compounds of the invention are those in which $R^1$ and $R^2$ have the meaning given above as in particular preferred and Het represents furyl.

The radical definitions listed above which are general or specified in preferred ranges apply both to the end products of the formula (I) and to the starting materials or intermediates correspondingly required in each case for the preparation.

These radical definitions can be combined in any manner with one another, that is also between the specified ranges of preferred compounds.

Examples of the possible meanings of the grouping $$-N\begin{matrix}R^1\\R^2\end{matrix}$$

in the formula (I) are listed in Table 1 below.

TABLE 1-continued

Examples of the meaning of the grouping $$-N\begin{matrix}R^1\\R^2\end{matrix}$$

| $-N\begin{matrix}R^1\\R^2\end{matrix}$ | $-N\begin{matrix}R^1\\R^2\end{matrix}$ |
|---|---|
| $-N\begin{matrix}CH_3\\C_6H_5\end{matrix}$ | $-N\begin{matrix}C_2H_5\\C_6H_5\end{matrix}$ |
| $-N\begin{matrix}CH(CH_3)_2\\2\text{-F-}C_6H_4\end{matrix}$ | $-N\begin{matrix}CH(CH_3)_2\\3\text{-F-}C_6H_4\end{matrix}$ |
| $-N\begin{matrix}CH(CH_3)_2\\4\text{-Cl-}C_6H_4\end{matrix}$ | $-N\begin{matrix}CH_3\\2\text{-CH}_3\text{-}C_6H_4\end{matrix}$ |
| $-N\begin{matrix}CH(CH_3)_2\\4\text{-CH}_3\text{-}C_6H_4\end{matrix}$ | $-N\begin{matrix}CH(CH_3)_2\\4\text{-OCH}_3\text{-}C_6H_4\end{matrix}$ |
| $-N\begin{matrix}CH(CH_3)_2\\3\text{-CH}_3\text{-}C_6H_4\end{matrix}$ | $-N\begin{matrix}CH(CH_3)_2\\4\text{-CF}_3\text{-}C_6H_4\end{matrix}$ |
| $-N\begin{matrix}CH_3\\C_2H_5\end{matrix}$ | $-N\begin{matrix}CH_3\\C_3H_7\end{matrix}$ |
| $-N\begin{matrix}CH_3\\CH(CH_3)_2\end{matrix}$ | $-N\begin{matrix}CH_3\\C_4H_9\end{matrix}$ |

TABLE 1-continued

Examples of the meaning of the grouping $$-N\begin{matrix}R^1\\R^2\end{matrix}$$

| $-N\begin{matrix}R^1\\R^2\end{matrix}$ | $-N\begin{matrix}R^1\\R^2\end{matrix}$ |
|---|---|
| $-N\begin{matrix}CH_3\\CH_2CH(CH_3)_2\end{matrix}$ | $-N\begin{matrix}C_3H_7\\CHC_2H_5\\ \quad \vert\\ \quad CH_3\end{matrix}$ |
| $-N\begin{matrix}C_2H_5\\C_3H_7\end{matrix}$ | $-N\begin{matrix}C_2H_5\\CH(CH_3)_2\end{matrix}$ |
| $-N\begin{matrix}C_2H_5\\C_4H_9\end{matrix}$ | $-N\begin{matrix}C_2H_5\\CH_2CH(CH_3)_2\end{matrix}$ |
| $-N\begin{matrix}C_2H_5\\CHC_2H_5\\ \quad \vert\\ \quad CH_3\end{matrix}$ | $-N\begin{matrix}C_3H_7\\CH(CH_3)_2\end{matrix}$ |
| $-N\begin{matrix}C_2H_5\\c\text{-}C_6H_{11}\end{matrix}$ | $-N\begin{matrix}C_3H_7\\c\text{-}C_6H_{11}\end{matrix}$ |
| $-N\begin{matrix}CH(CH_3)_2\\c\text{-}C_6H_{11}\end{matrix}$ | $-N\begin{matrix}CH_3\\CH_2C_6H_5\end{matrix}$ |
| $-N\begin{matrix}C_2H_5\\CH_2C_6H_5\end{matrix}$ | $-N\begin{matrix}C_3H_7\\CH_2C_6H_5\end{matrix}$ |
| $-N\begin{matrix}CH(CH_3)_2\\CH_2C_6H_5\end{matrix}$ | $-N\begin{matrix}CH_3\\CH_2\text{-}4\text{-F-}C_6H_4\end{matrix}$ |

TABLE 1-continued

Examples of the meaning of the grouping $-N\begin{matrix}R^1\\R^2\end{matrix}$

| $-N\begin{matrix}CH_3\\CH_2-C_6H_4-Cl\text{ (4-Cl)}\end{matrix}$ | $-N\begin{matrix}CH_3\\CH_2-C_6H_4-Cl\text{ (3-Cl)}\end{matrix}$ |
| $-N\begin{matrix}CH_3\\CH_2-C_6H_4-Cl\text{ (2-Cl)}\end{matrix}$ | $-N\begin{matrix}C_2H_5\\CH_2-C_6H_4-F\text{ (4-F)}\end{matrix}$ |
| $-N\begin{matrix}CH(CH_3)_2\\CH_2-C_6H_4-F\text{ (4-F)}\end{matrix}$ | $-N\begin{matrix}C_2H_5\\CH_2-C_6H_4-Cl\text{ (4-Cl)}\end{matrix}$ |
| $-N\begin{matrix}CH(CH_3)_2\\CH_2-C_6H_4-Cl\text{ (4-Cl)}\end{matrix}$ | $-N\begin{matrix}CH_3\\C_6H_4-F\text{ (4-F)}\end{matrix}$ |
| $-N\begin{matrix}C_2H_5\\C_6H_4-F\text{ (4-F)}\end{matrix}$ | $-N\begin{matrix}CH_3\\C_6H_4-Cl\text{ (4-Cl)}\end{matrix}$ |
| $-N\begin{matrix}C_2H_5\\C_6H_4-Cl\text{ (4-Cl)}\end{matrix}$ | $-N\begin{matrix}CH_3\\C_6H_3(CH_3)(Cl)\text{ (2-CH}_3\text{, 3-Cl)}\end{matrix}$ |
| $-N\begin{matrix}CH_3\\C_6H_3(Cl)(F)\text{ (3-Cl, 4-F)}\end{matrix}$ | $-N\begin{matrix}CH_3\\C_6H_3(F)(F)\text{ (3-F, 4-F)}\end{matrix}$ |
| $-N\begin{matrix}CH(CH_3)_2\\C_6H_3(F)(F)\text{ (3-F, 4-F)}\end{matrix}$ | $-N\begin{matrix}CH(CH_3)_2\\C_6H_3(Cl)(F)\text{ (3-Cl, 4-F)}\end{matrix}$ |
| $-N\begin{matrix}CH_3\\C_6H_3(F)(F)\text{ (2-F, 4-F)}\end{matrix}$ | $-N\begin{matrix}CH(CH_3)_2\\C_6H_3(F)(F)\text{ (2-F, 4-F)}\end{matrix}$ |
| $-N\begin{matrix}CH_3\\C_6H_3(CH_3)_2\text{ (3,5-(CH}_3)_2\text{)}\end{matrix}$ | $-N\begin{matrix}CH(CH_3)_2\\C_6H_4-CF_3\text{ (4-CF}_3\text{)}\end{matrix}$ |
| $-N\begin{matrix}CH_3\\C_6H_4-CF_3\text{ (3-CF}_3\text{)}\end{matrix}$ | $-N\begin{matrix}CH_3\\C_6H_3(CF_3)_2\text{ (3,5-(CF}_3)_2\text{)}\end{matrix}$ |
| $-N\begin{matrix}CH_3\\C_6H_3(CH_3)_2\text{ (2,4-(CH}_3)_2\text{)}\end{matrix}$ | $-N\begin{matrix}CH(CH_3)_2\\C_6H_3(F)(F)\text{ (3,5-F}_2\text{)}\end{matrix}$ |

TABLE 1-continued

Examples of the meaning of the grouping $-N\begin{smallmatrix}R^1\\R^2\end{smallmatrix}$

| $-N\begin{smallmatrix}R^1\\R^2\end{smallmatrix}$ | $-N\begin{smallmatrix}R^1\\R^2\end{smallmatrix}$ |
|---|---|
| $-N$(CH(CH$_3$)$_2$)(3,4-dichlorophenyl) | $-N$(CH(CH$_3$)$_2$)(3,4-dimethylphenyl) |
| $-N$(CH$_3$)(3,5-dichlorophenyl) | $-N$(CH$_3$)(CH$_2$CH$_2$CN) |
| $-N$(C$_2$H$_5$)(CH$_2$CH$_2$CN) | $-N$(CH$_2$CH$_2$CN)$_2$ |
| $-N$(CH(CH$_3$)$_2$)(CH$_2$CH$_2$OCH$_3$) | $-N$(C$_2$H$_5$)(CH$_2$CH$_2$OCH$_3$) |
| $-N$(CH$_3$)(CH$_2$CH$_2$OCH$_3$) | $-N$(CH$_3$)(OC$_2$H$_5$) |
| $-N$(CH$_3$)(OC$_3$H$_7$) | $-N$(CH$_3$)(OC$_4$H$_9$) |
| $-N$(C$_2$H$_5$)(OC$_2$H$_5$) | $-N$(C$_2$H$_5$)(OC$_3$H$_7$) |
| $-N$(C$_2$H$_5$)(OC$_4$H$_9$) | $-N$(C$_3$H$_7$)(OC$_3$H$_7$) |
| $-N$(C$_3$H$_7$)(OC$_4$H$_9$) | $-N$(CH(CH$_3$)$_2$)(OC$_2$H$_5$) |

TABLE 1-continued

Examples of the meaning of the grouping $-N\begin{smallmatrix}R^1\\R^2\end{smallmatrix}$

| $-N\begin{smallmatrix}R^1\\R^2\end{smallmatrix}$ | $-N\begin{smallmatrix}R^1\\R^2\end{smallmatrix}$ |
|---|---|
| $-N$(CH(CH$_3$)$_2$)(OC$_3$H$_7$) | $-N$(CH(CH$_3$)$_2$)(OCH$_2$CH$_2$OCH$_3$) |
| $-N$(CH$_3$)(3-chlorophenyl) | $-N$(CH$_3$)(4-methylphenyl) |
| $-N$(CH(CH$_3$)$_2$)(3-chlorophenyl) | $-N$(C$_3$H$_7$-n)(OCH(CH$_3$)$_2$) |
| $-N$(CH(CH$_3$)$_2$)(4-methylphenyl) | $-N$(CH$_3$)(2-methoxyphenyl) |
| $-N$(CH(CH$_3$)$_2$)(O—CH(CH$_3$)$_2$) | $-N$(CH(CH$_3$)$_2$)(3-trifluoromethylphenyl) |
| 2,6-dimethylmorpholino | $-N$(CH(CH$_3$)$_2$)(3,5-dichlorophenyl) |

TABLE 1-continued

Examples of the meaning of the grouping

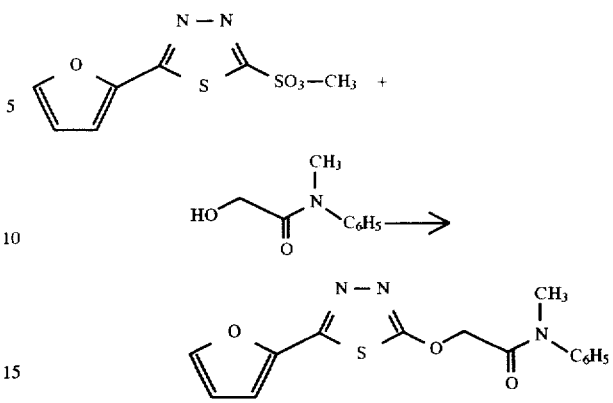

If, for example, 2-furyl-5-methylsulphonyl- 1,3,4-thiadiazole and N-methyl-hydroxyacetanilide are used as starting materials, the course of the reaction in the process of the invention can be sketched by the following formula scheme:

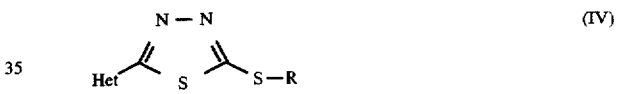

The alkylsulphonyl-1,3,4-thiadiazole derivatives to be used as starting materials in the process of the invention for the preparation of the compounds of the general formula (I) are generally defined by the formula (II). In the formula (II). Het preferably or in particular has the meaning which has already been given above as preferred or as in particular preferred for Het in connection with the description of the compounds of the formula (I); R preferably represents methyl or ethyl.

The starting materials of the formula (II) are not yet disclosed in the literature; they are also subject-matter of the present application as novel substances.

The novel alkylsulphonyl1,3,4-thiadiazole derivatives of the formula (II) arc obtained if alkylthio-1,3,4-thiadiazole derivatives of the general formula (IV)

 (IV)

in which

Het and R have the meaning given above, are reacted with an oxidizing agent. eg. hydrogen peroxide, at temperatures between $-20°$ C. and $+100°$ C. in the presence of absence of a catalyst, such as sodium molybdate, and in the presence or absence of a diluent, such as water and formic acid (cf. the Preparation Examples).

The precursors of the formula (IV) are not yet disclosed in the literature; they are likewise subject-matter of the present application as novel substances.

The novel alkylthio-1,3,4-thiadiazole derivatives of the formula (IV) are obtained if carboxylic acid halides of the general formula (V)

Het—CO—X (V)

in which

Het has the meaning given above and

X represents halogen (in particular chlorine), are reacted with methyl dithiocarbazate of the formula (VI)

$H_2N$—NH—CS—S—$CH_3$ (VI)

at temperatures between $0°$ C. and $100°$ C. in the presence or absence of a diluent, such as dioxane (cf. the Preparation Examples).

The starting materials of the formulae (V) and (VI) are known synthesis chemicals.

The hydroxyacetamides to be further used as starting materials in the process of the invention for the preparation of compounds of the formula (I) are generally defined by the formula (III).

In formula (III), R¹ and R² preferably or in particular have the meanings which have already been preferably given or given as preferred in particular for R¹ and R² above in connection with the description of the novel compounds of the formula (I).

The hydroxyacetamides of the formula (III) are known and/or can be prepared by processes known per se (cf. U.S. Pat. No. 4509971 and U.S. Pat. No. 4645525; in addition U.S. Pat. No. 4334073, DE-OS (German Published Specification) 3038598, DE-OS (German Published Specification) 3038636, EP-A 37526, EP-A 348737, DE-OS (German Published Specification) 3819477).

The process of the invention for the preparation of the novel heterocyclyl-1,3,4-thiazolyloxy-acetamides of the formula (I) is preferably carried out with the use of diluents. These preferably include hydrocarbons, such as toluene, xylene or cyclohexane, halogenated hydrocarbons, such as methylene chloride, ethylene chloride, chloroform or chlorobenzene, ethers such as diethyl ether, dipropyl ether, diisopropyl ether, dibutyl ether, diusobutyl ether, glycol dimethyl ether, tetrahydrofuran and dioxane, alcohols such as methanol, ethanol, propanol, isopropanol, butanol, isobutanol, sec-butanol or tert-butanol, ketones such as acetone, methyl ethyl ketone, methyl isopropyl ketone and methyl isobutyl ketone, esters such as methyl acetate and ethyl acetate, amides such as dimethylformamide, dimethylacetamide and N-methyl-pyrrolidone, nitriles such as acetonitrile and propionitrile, sulphoxides, such as dimethyl sulphoxide, and water or aqueous salt solutions.

The salts used in this case are preferably chlorides or sulphates of alkali metals or alkaline earth metals, such as sodium chloride, potassium chloride or calcium chloride. Particular preference is given to sodium chloride.

The process of the invention is advantageously carried out using acid acceptors. As these, use is preferably made of strongly basic alkali metal compounds and alkaline earth metal compounds, for example oxides, such as sodium oxide, potassium oxide, magnesium oxide and calcium oxide, hydroxides such as sodium hydroxide, potassium hydroxide, magnesium hydroxide and calcium hydroxide, alkoxides, such as sodium tert-butoxide and potassium tert-butoxide and/or carbonates, such as sodium carbonate, potassium carbonate, magnesium carbonate and calcium carbonate.

The addition of 0.01 to 10% by weight (based on glycolamide used of the formula (III)) of a phase transfer catalyst may prove advantageous in some cases. Examples of such catalysts which may be mentioned are:

tetrabutylammonium chloride, tetrabutylammonium bromide, tributylmethylphosphonium bromide, trimethyl-$C_{13}/C_{15}$-alkyl-ammonium chloride, dibenzyldimethylammonium methyl sulphate, dimethyl-$C_{12}/C_{14}$-alkyl-benzylammonium chloride, tetrabutylammonium hydroxide, 18-crown-6, triethylbenzylammonium chloride, trimethylbenzylammonium chloride, tetraethylammonium bromide.

The reaction temperatures can be varied in a relatively broad range in the process of the invention. Generally, temperatures between −50° C. and +110° C. are employed, preferably temperatures between −20° C. and +80° C.

The process of the invention is generally carried out at atmospheric pressure; however, it can also be carried out at elevated or reduced pressure, for instance between 0.1 and 10 bar.

To carry out the process of the invention, generally 0.5 to 5 mol, preferably 0.8 to 1.5 mol, of hydroxyacetamide of the formula (III) are used per mole of alkylsulphonyl-1,3,4-thiadiazole of the formula (II). The reaction components can be added in any order.

The reaction mixture is stirred in each case until the end of the reaction and the mixture is worked up by conventional methods (cf. the Preparation Examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants: Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds according to the invention of the formula (I) are suitable, especially, for selective control of monocotyledon and dicotyledon weeds in dicotyledon crops, especially in the pre-emergence process.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example anilides, for example diflufenican and propanil; arylcarboxylic acids, for example dichloropicolinic acid, dicamba and picloram; aryloxyalkanoic acids, for example 2,4-D, 2,4-DB, 2,4-DP, fluroxypyr, MCPA, MCPP and triclopyr; aryloxy-phenoxy-alkanoic esters, for example diclofop-methyl, fenoxaprop-ethyl, fluazifop-butyl, haloxyfop-methyl and quizalofop-ethyl; azinones, for example chloridazon and norflurazon; carbamates, for example chlorpropham, desmedipham, phenmedipham and propham; chloroacetanilides, for example alachlor, acetochlor, butachlor, metazachlor, metolachlor, pretilachlor and propachlor; dinitroanilines, for example oryzalin, pendimethalin and trifluralin; diphenyl ethers, for example acifluorfen, bifenox, fluoroglycofen, fomesafen, halosafen, lactofen and oxyfluorfen; ureas, for example chlortoluron, diuron, fluometuron, isoproturon, linuron and methabenzthiazuron; hydroxylamines, for example alloxydim, clethodim, cycloxydim, sethoxydim and tralkoxydim; imidazolinones, for example imazethapyr, imazamethabenz, imazapyr and imazaquin; nitriles, for example bromoxynil, dichlobenil and ioxynil; oxyacetamides, for example mefenacet; sulphonylureas, for example amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, for example butylate, cycloate, diallate, EPTC, esprocarb, molinate, prosulfocarb, thiobencarb and triallate; triazines, for example atrazine, cyanazine, simazine, simetryne, terbutryne and terbutylazin; triazinones, for example hexazinone, metamitron and metribuzin; others, for example aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and soil conditioners,are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the examples which follow.

PREPARATION EXAMPLES

Example 1

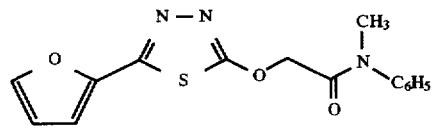

A mixture of 6.1 g (25 mmol) of 2-(2-furyl)-5-methylsulphonyl-1,3,4-thiadiazole, 4.1 g (25 mmol) of N-methyl-hydroxyacetanilide and 50 ml of acetone is cooled to −15° C. and, at this temperature, a solution of 1.2 g (30 mmol) of sodium hydroxide in 5 ml of water is added dropwise. The reaction mixture is stirred for 15 hours at −15° C. and then poured into water. The product formed in the crystalline state in the course of this is isolated by filtering off with suction.

6.6 g (78% of theory) of N-methyl-α-(2-(2-furyl)-1,3,4-thiadiazol-5-yl-oxy)-acetanilide of melting point 94° C. are obtained (from methylcyclohexane/ethyl acetate).

The compounds of the formula (I) listed in Table 2 below, for example, can also be prepared in a similar manner to Example 1 and according to the general description of the preparation process of the invention.

TABLE 2

Examples of the compounds of the formula (I)

$$\text{Het}-C(=N-N)-S-C(=...)-O-CH_2-C(=O)-N(R^1)(R^2)$$ (I)

| Example No. | Het— | —N(R¹)(R²) | Melting point (°C.) (Refractive index) |
|---|---|---|---|
| 2 | 2-furyl | N(CH(CH₃)₂)(4-F-C₆H₄) | 114 |
| 3 | 2-furyl | N(CH₃)(4-F-C₆H₄) | 89 |
| 4 | 2-furyl | N(CH₃)(2-CH₃-C₆H₄) | 114 |
| 5 | 2-furyl | N(CH₃)(2,3-(CH₃)₂-C₆H₃) | 106 |
| 6 | 2-furyl | N-(2-ethyl)piperidinyl | ($n_D^{20}$ = 1.5443) |
| 7 | 2-furyl | 1,2,3,4-tetrahydroquinolin-1-yl | 114 |
| 8 | 2-furyl | piperidin-1-yl | ($n_D^{20}$ = 1.5556) |
| 9 | 2-furyl | —N(C₂H₅)₂ | 64 |
| 10 | 2-furyl | —N(CH₂—CH=CH₂)₂ | 55 |
| 11 | 2-furyl | —N(C₄H₉-n)₂ | 60 |
| 12 | 2-furyl | N(CH₃)(3-CH₃-C₆H₄) | 70 |
| 13 | 2-furyl | —N(C₃H₇-n)₂ | ($n_D^{20}$ = 1.15156) |
| 14 | 2-furyl | —N(CH₃)(C₄H₉-n) | 60 |
| 15 | 2-furyl | N(CH₃)(3-CH₃-C₆H₄) | 110 |
| 16 | 2-furyl | N(CH₃)(cyclohex-1-enyl) | 115 |
| 17 | 2-furyl | N(CH(CH₃)₂)(OC₂H₄OC₂H₅) | ($n_D^{20}$ = 1.5324) |
| 18 | 2-furyl | N(CH(CH₃)₂)(C₆H₅) | 126 |
| 19 | 2-furyl | N(CH(CH₃)₂)(4-Cl-C₆H₄) | 105 |
| 20 | 2-furyl | N(C₂H₅)(4-F-C₆H₄) | 110 |
| 21 | 2-furyl | azocan-1-yl | 65 |

TABLE 2-continued

Examples of the compounds of the formula (I)

(I) Het—C(=N-N)—S—C(=O)—O—CH₂—C(=O)—N(R¹)(R²)

| Example No. | Het— | —N(R¹)(R²) | Melting point (°C.) (Refractive index) |
|---|---|---|---|
| 22 | 2-furyl | —N(CH₂CH(CH₃)₂)₂ (diisobutylamino) | 138 |
| 23 | 2-furyl | —N(CH(CH₃)₂)(3-CF₃-C₆H₄) | 125 |
| 24 | 2-furyl | —N(CH₃)—CH₂—(1,3-dioxolan-2-yl) | 60 |
| 25 | 2-furyl | —N(CH₂CH₂OCH₃)₂ | ($n_D^{20}$ = 1.5056) |
| 26 | 2-furyl | —N(CH₃)(4-Cl-C₆H₄) | 135 |
| 27 | 2-furyl | pyrrolidin-1-yl | 87 |
| 28 | 2-furyl | —N(CH(CH₃)₂)(4-OCH₃-C₆H₄) | 110 |
| 29 | 2-furyl | —N(CH(CH₃)(CH₂CH₃))(2-OCH₃-C₆H₄)(CH₃) | 115 |
| 30 | 2-furyl | —N(CH₃)—CH₂—C≡CH | 83 |
| 31 | 2-furyl | —N(C₂H₅)(C₆H₅) | 93 |
| 32 | 2-furyl | 3-ethylpiperidin-1-yl | ($n_D^{20}$ = 1.5407) |
| 33 | 2-furyl | —N(CH(CH₃)(CH₂CH₃))(2-CH₃-C₆H₄)(CH₃) | 117 |
| 34 | 2-furyl | —N(CH(CH₃)(CH₂CH₃))(2-OCH₃-5-Cl-C₆H₃)(CH₃) | 137 |
| 35 | 2-furyl | 2,4-dimethylpiperidin-1-yl | ($n_D^{20}$ = 1.5222) |
| 36 | 2-furyl | —N(CH₃)—CH₂—(2-methyltetrahydrofuran-2-yl) | ($n_D^{20}$ = 1.5115) |
| 37 | 2-furyl | —N(CH₃)(2-CH₃-C₆H₄) | 90 |
| 38 | 2-furyl | —N(CH(OCH₃)(CH(CH₃)(CH₂CH₃)))—CH₃ | ($n_D^{20}$ = 1.5367) |
| 39 | 2-furyl | —N(CH₃)(CH₂CF₃) | 86 |
| 40 | 2-furyl | —N(CH(CH₃)₂)(4-CH₃-C₆H₄) | 69 |

TABLE 2-continued

Examples of the compounds of the formula (I)

$$\text{Het} \overset{N-N}{\underset{S}{\diagdown\!\diagup}} O \diagdown\!\!\diagup \overset{R^1}{\underset{O}{N-R^2}} \quad (I)$$

$$-N \overset{R^1}{\underset{R^2}{\diagdown}}$$

| Example No. | Het— | $-N\overset{R^1}{\underset{R^2}{\diagdown}}$ | Melting point (°C.) (Refractive index) |
|---|---|---|---|
| 41 | 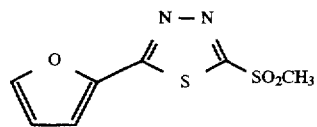 | $-N\overset{CH(CH_3)_2}{\underset{}{\diagdown}}\!\!\diagup\!\!\diagdown\!\!\overset{CF_3}{\underset{CF_3}{}}$ | 141 |

Starting materials of the formula (II):

Example (II-1)

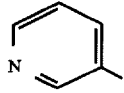

170 g (0.86 mol) of 2-(2-furyl)-5-methylthio-1,3,4-thiadiazole are introduced, together with 2 g of sodium tungstate, in 250 ml of acetic acid. 315 ml (3.1 mol) of 30% strength hydrogen peroxide are added to this dropwise at 45° C. The mixture is further stirred for one hour at 45° C. and a further 80 ml of 30% strength hydrogen peroxide is additionally added dropwise. The mixture is then further stirred for 3 hours at 45° C., cooled and the solids are filtered off with suction. The solids are washed with a sparing amount of water and dried.

195 g (63% of theory) of 2-(2-furyl)-5-methylsulphonyl-1,3,4-thiadiazole of melting point 120° C. are obtained.

In a similar manner to Example (II-1), the compounds of the formula (II) listed in Table 3 below can also be prepared, for example.

TABLE 3

Examples of the compounds of the formula (II)

$$\text{Het}\overset{N-N}{\underset{S}{\diagdown\!\diagup}} SO_2R \quad (II)$$

| Example No. | Het— | R | Melting point (°C.) |
|---|---|---|---|
| II-2 | 2-Cl-pyridyl | CH₃ | 175 |
| II-3 | pyridyl | CH₃ | |

TABLE 3-continued

Examples of the compounds of the formula (II)

$$\text{Het}\overset{N-N}{\underset{S}{\diagdown\!\diagup}} SO_2R \quad (II)$$

| Example No. | Het— | R | Melting point (°C.) |
|---|---|---|---|
| II-4 | 2-pyridyl | CH₃ | |
| II-5 | 3-pyridyl | CH₃ | |
| II-6 | 2-H₃C-5-pyrimidinyl (H₃C on pyridine) | CH₃ | |
| II-7 | 2,3-dimethylpyridyl | CH₃ | |
| II-8 | 2-Cl-pyridyl | CH₃ | |
| II-9 | 2,3-Cl₂-pyridyl | CH₃ | |
| II-10 | 3-NO₂-pyridyl | CH₃ | |
| II-11 | H₃C-pyrazinyl | CH₃ | |
| II-12 | pyridazinyl | CH₃ | |
| II-13 | 3-CH₃-furyl | CH₃ | |
| II-14 | 2,5-(CH₃)₂-furyl | CH₃ | |
| II-15 | 2,5-(CH₃)₂-3-CH₃-furyl | CH₃ | |

Starting materials of the formula (IV):

Example (IV-1)

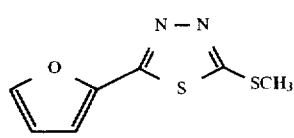

220 g (1.8 mol) of S-methyl dithiocarbazate are introduced in 1000 ml of dioxane. 266 g (2 mol) of furan-2-carbonyl chloride are added dropwise at room temperature (20° C.). The temperature increases to 40° C. in the course of this. The mixture is then further stirred for 30 minutes at 70° C. The reaction batch is cooled and the precipitated beige solid is filtered off with suction.

298 g (84% of theory) of 2-(2-furyl)-5-methylthio-1,3,4-thiadiazole of melting point 128° C. are obtained.

Example (IV-2)

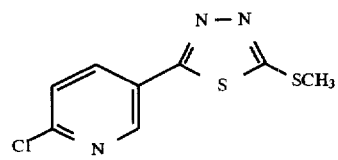

244 g (2.0 mol) of S-methyl dithiocarbazate are introduced together with 158 g (2.0 mol) of pyridine in 825 ml of diethylene glycol dimethyl ether ("diglyme"). To this mixture cooled to −5° C. is added dropwise a solution of 360 g (2.0 mol) of 6-chloro-nicotinyl chloride in 445 ml of diethylene glycol dimethyl ether. After stirring for 30 minutes, 444 ml of concentrated sulphuric acid are added dropwise at 0° C. to +5° C. and the mixture is stirred for 15 hours at 20° C. The mixture is then poured onto ice and the product formed in the crystalline state is isolated by filtering off with suction.

402 g (82% of theory) of 2-(6-chloro-pyridin-3-yl)-5-methylthio-1,3,4-thiadiazole of melting point 136° C. are obtained.

The compounds of the formula (IV) listed in Table 4 below, for example, can also be prepared in a similar manner to the Examples (IV-1) and (IV-2).

TABLE 4

Examples of the compounds of the formula (IV)

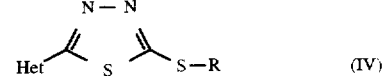

| Example No. | Het- | R | Melting point (°C.) |
|---|---|---|---|
| IV-3 | pyridin-2-yl | CH$_3$ | |
| IV-4 | pyridin-3-yl | CH$_3$ | |

TABLE 4-continued

Examples of the compounds of the formula (IV)

| Example No. | Het- | R | Melting point (°C.) |
|---|---|---|---|
| IV-5 | pyridin-3-yl | CH$_3$ | |
| IV-6 | 2-methylthio-pyridin-5-yl | CH$_3$ | |
| IV-7 | 6-methyl-pyridin-3-yl | CH$_3$ | |
| IV-8 | 2-methyl-pyridin-5-yl | CH$_3$ | |
| IV-9 | 2-methyl-pyrazin-5-yl | CH$_3$ | |
| IV-10 | 3-methyl-furan-2-yl | CH$_3$ | |
| IV-11 | 5-methyl-furan-2-yl | CH$_3$ | |
| IV-12 | pyridazin-3-yl | CH$_3$ | |
| IV-13 | 2-chloro-pyridin-5-yl | CH$_3$ | |
| IV-14 | 2,3-dichloro-pyridin-5-yl | CH$_3$ | |
| IV-15 | 3,5-dimethyl-furan-2-yl | CH$_3$ | |
| IV-16 | 5-nitro-pyridin-3-yl | CH$_3$ | |

Use Examples:
Example A
Pre-emergence Test
Solvent: 5 parts by weight of acetone
Emulsifier: 1 part by weight of alkylaryl polyglycol ether To produce an expedient active compound preparation, 1 part by weight of active compound is mixed with the specified amount of solvent, the specified amount of emulsifier is added and the concentrate is diluted with water to the desired concentration.

Seeds of the test plants are sowed in normal soil. After 24 hours, the soil is watered with the active compound preparation. The amount of water per unit area is expediently kept constant in this. The active compound concentration in the preparation is of no importance; the only critical factor is the application rate of the active compound per unit area. After three weeks, the degree of damage of the plants is evaluated in % damage in comparison with the development of the untreated control. In the evaluation:

0%=no effect (as untreated control)
100%=total destruction

In this test, the compound according to Preparation Example 1, for example, showed, with good compatibility with crops, for example soya and cotton, high activity against weeds. The same also applies to the compounds according to Preparation Examples 7, 17, 20 and 21 (cf. the following Tables A-1 and A-2).

$R^1$ represents hydrogen, $C_1$–$C_8$-alkyl optionally substituted by fluorine, chlorine, cyano or $C_1$–$C_4$-alkoxy, $C_2$–$C_8$-alkenyl optionally substituted by fluorine or chlorine, $C_2$–$C_8$-alkinyl or benzyl optionally substituted by fluorine, chlorine, $C_1$–$C_4$-alkyl or $C_1$–$C_4$-alkoxy, $R^2$ represents $C_1$–$C_8$-alkyl optionally substituted by fluorine, chlorine, cyano or $C_1$–$C_4$-alkoxy, $C_2$–$C_8$-alkenyl optionally substituted by fluorine or chlorine, $C_2$–$C_8$-alkinyl, $C_3$–$C_6$-cyclolkyl optionally substituted by chlorine or $C_1$–$C_3$-alkyl, $C_5$- or $C_6$-cycloalkenyl, benzyl optionally substituted by fluorine, chlorine, $C_1$–$C_4$-alkyl or $C_1$–$C_4$-alkoxy, phenyl optionally substituted by fluorine, chlorine, bromine, iodine, cyano, nitro, $C_1$–$C_4$-alkyl, trifluoromethyl, $C_1$–$C_4$-alkoxy or $C_1$–$C_4$-alkylthio, $C_1$–$C_8$-alkoxy optionally substituted by $C_1$–$C_4$-alkoxy, or $C_3$–$C_4$-alkenyloxy, or $R^1$ and $R^2$ together with the nitrogen atom to which they are bound form a saturated or unsaturated five- to seven-membered nitrogen heterocycle which is optionally monosubstituted to trisubstituted by $C_1$–$C_3$-alkyl and can additionally contain oxygen and is optionally benzo-fused, and Het represents in each case unsubstituted or substituted furyl, benzofuryl, tetrahydrofuryl, pyrrolyl, benzopyrrolyl, tetrahydropyrrolyl, oxazolyl,

TABLE A-1

Pre-emergence Test/Greenhouse

| Active compound | Application rate (g/ha) | Soya | Digitaria | Echinochloa | Setaria | Amaranthus | Chenopodium | Portulaca |
|---|---|---|---|---|---|---|---|---|
| 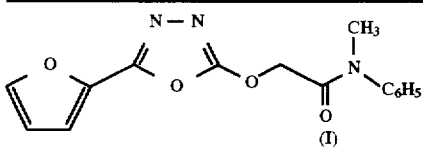 | 500 | 0 | 100 | 90 | 90 | 100 | 100 | 100 |

TABLE A-2

Pre-emergence Test/Greenhouse

| Active compound (according to Preparation Example) | Application rate (g/ha) | Soya | Cotton | Alopecurus | Cynodon | Digitaria | Panicum | Setaria |
|---|---|---|---|---|---|---|---|---|
| (1) | 500 | 0 | 0 | 60 | 100 | 100 | 80 | 90 |
| (7) | 500 | 10 | 0 | 60 | — | 95 | 95 | 95 |
| (17) | 500 | 0 | 0 | 100 | 100 | 100 | 100 | 100 |
| (20) | 500 | 0 | 0 | 90 | 100 | 95 | 60 | 90 |
| (21) | 500 | 0 | 0 | 90 | 100 | 90 | 60 | 95 |

We claim:

1. A heterocyclyl-1,3,4-thiadiazolyloxyacetamides of the formula (I)

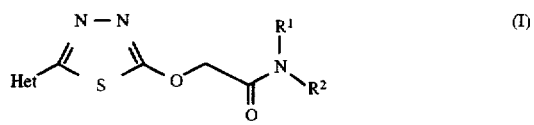

in which isoxazolyl, thiazolyl, isothiazolyl, oxadiazolyl, thiadiazolyl, pyridyl, pyrimidyl, triazinyl or tetrahydropyranyl, the substituents being selected from the group consisting of fluorine, chlorine, bromine, cyano in each case optionally fluorine- or chlorine-substituted methyl, ethyl n- or i-propyl, n-, i-, s- or t-butyl, methoxy, ethoxy n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl.

2. A compound of the formula (I) according to claim 1, in which
- $R^1$ represents methyl, ethyl, n- or i-propyl, n-, i- or s-butyl, n-, i- or s-pentyl each of which is optionally substituted by fluorine, chlorine, cyano, methoxy or ethoxy, propenyl, butenyl, propinyl or butinyl,
- $R^2$ represents methyl, ethyl, n- or i-propyl, n-, i- or s-butyl, n-, i- or s-pentyl, n-, i- or s-hexyl each of which is optionally substituted by fluorine, chlorine, cyano, methoxy or ethoxy; propenyl, butenyl, pentenyl, propinyl, butinyl or pentinyl; cyclopentyl or cyclohexyl each of which is optionally substituted by methyl, or ethyl; cyclohexenyl; benzyl which is optionally substituted by fluorine, chlorine or methyl; or phenyl which is optionally substituted in each case by fluorine, chlorine, bromine, cyano, nitro, methyl, ethyl, trifluoromethyl, methoxy or ethoxy; methoxy, ethoxy, n- or i-propoxy, n-, i- or s-butoxy, n-, i- or s-pentyloxy each of which is optionally substituted by methoxy or ethoxy, or
- $R^1$ and $R^2$ together with the nitrogen atom to which they are bound represent piperidinyl or morpholinyl which is optionally monosubstituted to trisubstituted by methyl or ethyl; pyrrolidinyl which is optionally monosubstituted or disubstituted by methyl and/or ethyl; perhydroazepinyl; or 1,2,3,4-tetrahydro(iso)-quinolinyl, and
- Het represents in each case unsubstituted or Substituted furyl, benzofuryl, tetrahydrofuryl, pyrrolyl, benzopyrrolyl, tetrahydropyrrolyl, oxazolyl, isoxazolyl, thiazolyl, isothiazolyl, oxadiazolyl, thiadiazolyl, pyridyl, pyrimidyl, triazinyl or tetrahydropyranyl, the substituents being selected from the group consisting of
  - fluorine, chlorine, bromine, cyano in each case optionally fluorine- or chlorine-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl.

3. A process for the preparation of heterocyclyl-1,3,4-thiadiazolyloxyacetamides of the formula (I) according to claim 1, comprising reacting alkylsulphonyl-1,3,4-thiadiazoles of the general formula (II)

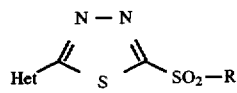

(II)

in which
Het represents in each case unsubstituted or substituted furyl, benzofuryl, tetrahydrofuryl, pyrrolyl, benzopyrrolyl, tetrahydropyrrolyl, oxazolyl, isoxazolyl, thiazolyl, isothiazolyl, oxadiazolyl, thiadiazolyl, pyridyl, pyrimidyl, triazinyl or tetrahydropyranyl, the substituents being selected from the group consisting of
  fluorine, chlorine, bromine, cyano in each case optionally fluorine- or chlorine-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl;
R represents alkyl,
are reacted with hydroxyacetamides of the general formula (III)

(III)

in which
- $R^1$ represents hydrogen, $C_1$–$C_8$-alkyl optionally substituted by fluorine, chlorine, cyano or $C_1$–$C_4$-alloxy, $C_2$–$C_8$-alkenyl optionally substituted by fluorine or chlorine, $C_2C_8$-alkinyl or benzyl optionally substituted by fluorine, chlorine, $C_1$–$C_4$-alkyl or $C_1$–$C_4$-alkoxy,
- $R^2$ represents $C_1$–$C_8$-alkyl optionally substituted by fluorine, chlorine, cyano or $C_1$–$C_4$-alkoxy, $C_2$–$C_8$-alkenyl optionally substituted by fluorine or chlorine, $C_2$–$C_8$-alkinyl, $C_3$–$C_6$-cycloalkyl optionally substituted by chlorine or $C_1$–$C_3$-alkyl, $C_5$- or $C_6$-cycloalkenyl, benzyl optionally substituted by fluorine, chlorine, $C_1$–$C_4$-alkyl or $C_1$–$C_4$-alkoxy, phenyl optionally substituted by fluorine, chlorine, bromine, iodine, cyano, nitro, $C_1$–$C_4$-alkyl, trifluoromethyl, $C_1$–$C_4$-alkoxy or $C_1$–$C_4$-alkylthio $C_1$–$C_8$-alkoxy optionally substituted by $C_1$–$C_4$-alkoxy, or $C_3$–$C_4$-alkenyloxy, or
- $R^1$ and $R^1$ together with the nitrogen atom to which they are bound form a saturated or unsaturated five- to seven-membered nitrogen heterocycle which is optionally monosubstituted to trisubstituted by $C_1$–$C_3$-alkyl and can additionally contain oxygen and is optionally benzo-fused, and in the presence or absence of a diluent, in the presence or absence of an acid acceptor and in the presence or absence of a catalyst.

4. An herbicidal composition comprising an herbicidally effective amount of a compound according to claim 1 and an extender.

5. A method of controlling unwanted plant growth which comprises administering to such plant growth an herbicidally effective amount of a compound according to claim 1.

6. A process for the preparation of herbicides, comprising mixing compounds of the general formula (I) according to claim 1 with extenders and surfactants.

7. Alkylsulphonyl-1,3,4-thiadiazoles of the formula (II),

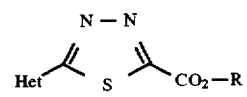

(II)

in which
Het represents in each case unsubstituted or substituted furyl, benzofuryl, tetrahydrofuryl, pyrrolyl, benzopyrrolyl, tetrahydropyrrolyl, oxazolyl, isoxazolyl, thiazolyl, isothiazolyl, oxadiazolyl, thiadiazolyl, pyrimidyl, triazinyl or tetrahydropyranyl, the substituents being selected from the group consisting of
  fluorine, chlorine, bromine, cyano in each case optionally fluorine- or chlorine-substituted methyl, ethyl, n- or i-propyl, n-, i-, s- or t-butyl, methoxy, ethoxy n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, and
R represents alkyl.

8. Alkylthio-1,3,4-thiadiazole derivatives of the formula (IV),

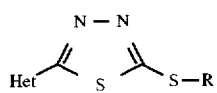

(IV)

in which

Het represents in each case unsubstituted or substituted furyl, benzofuryl, tetrahydrofuryl, pyrrolyl, benzopyrrolyl, tetrahydropyrrolyl, oxazolyl, isoxazolyl, thiazolyl, isothiazolyl, oxadiazolyl, thiadiazolyl, pyrimidyl, triazinyl or tetrahydropyranyl, the substituents being selected from the group consisting of fluorine, chlorine, bromine, cyano in each case optionally fluorine- or chlorine-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, and R represents alkyl.

* * * * *

UNITED STATES PATENT AND TRADEMARK OFFICE
CERTIFICATE OF CORRECTION

PATENT NO. : 5,780,392
DATED : July 14, 1998
INVENTOR(S) : Heinz Forster, et al.

It is certified that error appears in the above-identified patent and that said Letters Patent is hereby corrected as shown below:

Title Page [87] PCT Pub. No.  Delete "WO94" and substitute --WO95--

Col. 26, Line 10  Delete "$C_3$-$C_6$-cyclolkyl" and substitute --$C_3$-$C_6$-cycloalkyl--

Col. 28, Line 9  Delete "$C_1$-$C_4$-alloxy" and substitute --$C_1$-$C_4$-alkoxy--

Col. 28, Line 25  Delete "R' and R' together" and substitute --R1 and R2 together--

Col. 28, Line 45  Delete "Formula" and substitute --

--

Signed and Sealed this

Twenty-first Day of September, 1999

Attest:

Q. TODD DICKINSON

Attesting Officer    Acting Commissioner of Patents and Trademarks